(12) United States Patent
Solar et al.

(10) Patent No.: US 7,720,522 B2
(45) Date of Patent: May 18, 2010

(54) FIDUCIAL MARKER DEVICES, TOOLS, AND METHODS

(75) Inventors: Matthew S. Solar, Indialantic, FL (US); Thomas L. Bridges, Melbourne Beach, FL (US); David Lee, Melbourne Beach, FL (US); Mark Stephen Freas, Indialantic, FL (US)

(73) Assignee: Medtronic, Inc., Minneapolis, MN (US)

( * ) Notice: Subject to any disclaimer, the term of this patent is extended or adjusted under 35 U.S.C. 154(b) by 1933 days.

(21) Appl. No.: 10/374,677

(22) Filed: Feb. 25, 2003

(65) Prior Publication Data

US 2004/0167393 A1 Aug. 26, 2004

(51) Int. Cl.
*A61B 5/05* (2006.01)
(52) U.S. Cl. ........................ 600/426; 600/407; 600/410; 600/414; 600/424; 600/431; 378/20; 606/72; 606/130
(58) Field of Classification Search ................. 600/407, 600/410, 414, 431, 424, 426; 378/20; 606/130, 606/72
See application file for complete search history.

(56) References Cited

U.S. PATENT DOCUMENTS

| | | | |
|---|---|---|---|
| 2,650,588 | A | 9/1953 | Radcliffe |
| 4,228,799 | A | 10/1980 | Anichkov et al. |
| 4,408,372 | A | 10/1983 | Kimura et al. |
| D274,117 | S | 6/1984 | Lapps |
| 4,583,538 | A | 4/1986 | Onik et al. |
| 4,629,451 | A | 12/1986 | Winters et al. |
| 4,630,375 | A | 12/1986 | Spolyar |
| 4,675,173 | A | 6/1987 | Widder |
| 4,763,548 | A | 8/1988 | Leibinger et al. |
| D306,190 | S | 2/1990 | Poulsen et al. |

(Continued)

FOREIGN PATENT DOCUMENTS

DE 9112356 2/1992

(Continued)

OTHER PUBLICATIONS

"Acustar", *Z-KAT Inc.*, http://www.z-kat.com/acustar.htm,(2002),5 pages.

(Continued)

*Primary Examiner*—Brian Casler
*Assistant Examiner*—James Kish
(74) *Attorney, Agent, or Firm*—Harness, Dickey & Pierce, PLC

(57) ABSTRACT

This document discusses, among other things, fiducial marker devices, tools, and methods. One example illustrates a combined imagable fiducial locator and divot for receiving a positioning wand of an image-guided surgical (IGS) workstation. A further example is reflective such that it is locatable by a remote detector of an optical positioning system. A generally cylindrical (e.g., faceted cylindrical) columnar locator permits easy application of reflective tape. Other examples discusses a unitary fiducial marker with multiple divots and a swiveling and/or tilted fiducial marker divot, each of which allows manipulation of a positioning wand into a remote camera's field of view. Another example includes at least one reflector that can be aimed. A further example discusses an imagable fiducial marker carrier that is attachable to a single location on a patient's skull to reduce trauma. A keying arrangement fixedly defines the orientation of the carrier, allowing detachment and reattachment in the same orientation.

22 Claims, 14 Drawing Sheets

U.S. PATENT DOCUMENTS

| | | | |
|---|---|---|---|
| 4,931,056 A | 6/1990 | Ghajar et al. | |
| 4,943,293 A | 7/1990 | Lee, Jr. | |
| 4,943,298 A | 7/1990 | Fujita et al. | |
| 4,945,914 A | 8/1990 | Allen | |
| 4,954,914 A | 9/1990 | Karita et al. | |
| 4,991,579 A | 2/1991 | Allen | |
| 5,016,639 A | 5/1991 | Allen | |
| 5,042,462 A | 8/1991 | Bremer | |
| 5,058,580 A | 10/1991 | Hazard | |
| 5,094,241 A | 3/1992 | Allen | |
| 5,098,435 A | 3/1992 | Stednitz et al. | |
| 5,119,817 A | 6/1992 | Allen | |
| 5,142,930 A * | 9/1992 | Allen et al. | 74/469 |
| 5,178,164 A | 1/1993 | Allen | |
| 5,186,174 A | 2/1993 | Schlondorff et al. | |
| 5,197,476 A | 3/1993 | Nowacki et al. | |
| 5,201,737 A | 4/1993 | Leibinger et al. | |
| 5,211,164 A | 5/1993 | Allen | |
| 5,222,499 A | 6/1993 | Allen et al. | |
| 5,230,338 A | 7/1993 | Allen et al. | |
| 5,263,980 A | 11/1993 | Leibinger et al. | |
| 5,299,253 A | 3/1994 | Wessels | |
| 5,300,075 A | 4/1994 | Gordon | |
| 5,300,076 A | 4/1994 | Leriche et al. | |
| 5,305,203 A | 4/1994 | Raab et al. | |
| 5,368,030 A * | 11/1994 | Zinreich et al. | 600/414 |
| 5,383,454 A | 1/1995 | Bucholz | |
| 5,389,101 A | 2/1995 | Heilbrun et al. | |
| 5,394,457 A | 2/1995 | Leibinger et al. | |
| 5,394,875 A | 3/1995 | Lewis et al. | |
| 5,397,329 A * | 3/1995 | Allen | 606/73 |
| 5,417,692 A | 5/1995 | Goble et al. | |
| 5,468,242 A | 11/1995 | Reisberg et al. | |
| 5,469,847 A | 11/1995 | Zinreich et al. | |
| 5,494,034 A | 2/1996 | Schlondorff et al. | |
| 5,551,429 A | 9/1996 | Fitzpatrick et al. | |
| 5,566,081 A | 10/1996 | Yoshizawa et al. | |
| 5,575,794 A | 11/1996 | Walus et al. | |
| 5,590,215 A | 12/1996 | Allen | |
| 5,595,193 A | 1/1997 | Walus et al. | |
| 5,603,318 A | 2/1997 | Heilbrun et al. | |
| 5,636,255 A | 6/1997 | Ellis | |
| 5,681,313 A | 10/1997 | Diez et al. | |
| 5,683,217 A | 11/1997 | Walther et al. | |
| 5,730,130 A | 3/1998 | Fitzpatrick et al. | |
| 5,743,899 A | 4/1998 | Zinreich | |
| 5,769,789 A | 6/1998 | Wang et al. | |
| 5,799,099 A | 8/1998 | Wang et al. | |
| 5,807,252 A | 9/1998 | Hassfeld et al. | |
| 5,807,396 A | 9/1998 | Raveh et al. | |
| 5,836,954 A | 11/1998 | Heilbrun et al. | |
| 5,851,183 A | 12/1998 | Bucholz | |
| 5,860,389 A | 1/1999 | Caldwell | |
| 5,871,445 A | 2/1999 | Bucholz | |
| 5,891,034 A | 4/1999 | Bucholz | |
| 5,916,164 A | 6/1999 | Fitzpatrick et al. | |
| 5,954,722 A | 9/1999 | Bono | |
| 5,957,934 A | 9/1999 | Rapoport | |
| 5,968,047 A | 10/1999 | Reed | |
| 5,984,930 A | 11/1999 | Maciunas et al. | |
| 6,000,892 A | 12/1999 | Takasaki | |
| 6,006,126 A | 12/1999 | Cosman | |
| 6,011,987 A * | 1/2000 | Barnett | 600/414 |
| 6,019,776 A | 2/2000 | Preissman et al. | |
| 6,052,477 A | 4/2000 | Wang et al. | |
| 6,071,291 A | 6/2000 | Forst et al. | |
| 6,073,044 A | 6/2000 | Fitzpatrick et al. | |
| 6,076,008 A | 6/2000 | Bucholz | |
| 6,082,366 A | 7/2000 | Andra et al. | |
| 6,096,048 A | 8/2000 | Howard, III et al. | |
| 6,102,914 A | 8/2000 | Bulstra et al. | |
| 6,146,390 A | 11/2000 | Heilbrun et al. | |
| 6,165,181 A | 12/2000 | Heilbrun et al. | |
| 6,167,295 A | 12/2000 | Cosman | |
| 6,168,780 B1 | 1/2001 | Andra | |
| 6,181,960 B1 | 1/2001 | Jensen et al. | |
| 6,187,018 B1 | 2/2001 | Sanjay-Gopal et al. | |
| 6,206,890 B1 * | 3/2001 | Truwit | 606/130 |
| 6,226,548 B1 * | 5/2001 | Foley et al. | 600/426 |
| 6,236,875 B1 | 5/2001 | Bucholz et al. | |
| 6,241,732 B1 * | 6/2001 | Overaker et al. | 606/327 |
| 6,261,300 B1 | 7/2001 | Carol et al. | |
| 6,273,896 B1 | 8/2001 | Franck et al. | |
| 6,282,437 B1 | 8/2001 | Franck et al. | |
| 6,298,262 B1 | 10/2001 | Franck et al. | |
| 6,304,768 B1 | 10/2001 | Blume et al. | |
| 6,306,126 B1 | 10/2001 | Moctezuma et al. | |
| 6,327,491 B1 * | 12/2001 | Franklin et al. | 600/429 |
| 6,333,971 B2 * | 12/2001 | McCrory et al. | 378/162 |
| 6,351,659 B1 * | 2/2002 | Vilsmeier | 600/407 |
| 6,351,662 B1 | 2/2002 | Franck et al. | |
| 6,381,485 B1 | 4/2002 | Hunter et al. | |
| 6,382,815 B1 | 5/2002 | Klearman et al. | |
| 6,402,757 B1 | 6/2002 | Moore, III et al. | |
| 6,405,072 B1 | 6/2002 | Cosman | |
| 6,419,680 B1 * | 7/2002 | Cosman et al. | 606/130 |
| 6,430,434 B1 * | 8/2002 | Mittelstadt | 600/426 |
| 6,454,769 B2 | 9/2002 | Wagner et al. | |
| 6,459,927 B1 | 10/2002 | Franklin et al. | |
| 6,464,706 B1 | 10/2002 | Winters | |
| 6,499,488 B1 * | 12/2002 | Hunter et al. | 128/899 |
| 6,546,277 B1 * | 4/2003 | Franck et al. | 600/426 |
| 6,565,573 B1 | 5/2003 | Ferrante et al. | |
| 6,694,168 B2 | 2/2004 | Traxel et al. | |
| 6,738,657 B1 | 5/2004 | Franklin et al. | |
| D493,198 S | 7/2004 | Starkel | |
| 6,865,907 B2 | 3/2005 | Andrews et al. | |
| 6,866,666 B1 | 3/2005 | Sinnott et al. | |
| 6,942,667 B1 * | 9/2005 | Song | 606/72 |
| RE39,133 E * | 6/2006 | Clayton et al. | 600/426 |
| D527,820 S | 9/2006 | Solar et al. | |
| D528,211 S | 9/2006 | Solar et al. | |
| 2001/0000186 A1 | 4/2001 | Bramlet et al. | |
| 2001/0004395 A1 | 6/2001 | McCrory et al. | |
| 2001/0010004 A1 | 7/2001 | Traxel et al. | |
| 2001/0027271 A1 | 10/2001 | Franck et al. | |
| 2001/0051807 A1 | 12/2001 | Grafton | |
| 2002/0028423 A1 | 3/2002 | Levisman | |
| 2002/0052610 A1 | 5/2002 | Skakoon et al. | |
| 2002/0156363 A1 * | 10/2002 | Hunter et al. | 600/410 |
| 2003/0040753 A1 | 2/2003 | Daum et al. | |
| 2003/0187351 A1 | 10/2003 | Franck et al. | |
| 2004/0019265 A1 * | 1/2004 | Mazzocchi et al. | 600/407 |
| 2004/0019365 A1 * | 1/2004 | Ding et al. | 607/17 |
| 2004/0030236 A1 * | 2/2004 | Mazzocchi et al. | 600/414 |
| 2004/0030237 A1 | 2/2004 | Lee et al. | |
| 2004/0078084 A1 | 4/2004 | Albertorio | |
| 2004/0122305 A1 * | 6/2004 | Grimm et al. | 600/407 |
| 2004/0167391 A1 * | 8/2004 | Solar et al. | 600/411 |
| 2004/0167393 A1 | 8/2004 | Solar et al. | |
| 2004/0254581 A1 | 12/2004 | Leclair | |
| 2005/0015032 A1 | 1/2005 | Stein | |
| 2005/0042574 A1 | 2/2005 | Lazarof | |
| 2005/0043735 A1 | 2/2005 | Ahmad | |
| 2007/0225599 A1 | 9/2007 | Solar et al. | |

FOREIGN PATENT DOCUMENTS

| | | |
|---|---|---|
| EP | 0787467 A1 | 8/1997 |
| EP | 0813846 A1 | 12/1997 |
| EP | 0820736 A1 | 1/1998 |
| EP | 1033113 A1 | 9/2000 |
| EP | 1249207 A2 | 10/2002 |
| RU | 2026648 | 1/1995 |

| | | | |
|---|---|---|---|
| WO | WO 9709929 A1 | 3/1997 | |
| WO | WO 9838908 A1 | 9/1998 | |
| WO | WO 9911998 A1 | 3/1999 | |
| WO | WO 9916352 A1 | 4/1999 | |
| WO | WO 9940869 A1 | 8/1999 | |
| WO | WO-0149197 | 7/2001 | |
| WO | WO 0178015 A2 | 10/2001 | |
| WO | WO-2004075768 | 9/2004 | |
| WO | WO-2004075768 A3 | 9/2004 | |

OTHER PUBLICATIONS

"Bone Anchor", U.S. Appl. No. 10/405,881, filed Apr. 2, 2003.

"Multi-Modality Radiographic Markers", *IZI Medical Products*, http://www.izimed.com,(2002),pp. 1-12.

"Stryker Navigation System, The Smarter Vision—Image Guided Surgery", *Stryker Leibinger Inc.*, (2002),8 pages.

Solar, M.S., et al., "Fiducial Marker", U.S. Appl. No. 29/199,249, filed Feb. 12, 2004.

U.S. Appl. No. 10/206,884, filed Jul. 29, 2002, Fiducial Marker Devices, Tools, and Methods.

U.S. Appl. No. 10/454,145, filed Jun. 4, 2003, Fiducial Marker Devices, Tools, and Methods.

U.S. Appl. No. 10/454,786, filed Jun. 4, 2003, Fiducial Marker Devices, and Methods.

U.S. Appl. No. 10/688,801, filed Oct. 17, 2003, Fiducial Marker Devices, Tools, and Methods.

U.S. Appl. No. 11/689,356, filed Mar. 21, 2007, Fiducial Marker Devices, Tools, and Methods.

Clarysse, P. et al. "A Computer-Assisted System for 3-D Frameless Localization in Stereotaxic MRI", IEEE Transactions on Medical Imaging, 10, (1991) 523-529.

Coste, E. et al., "Frameless Method of Sterotaxic Localization with DSA", Radiology, (1993), 829-834.

Leibinger et al., "Microsurgical Neurectomy Bayonet Scissors", The Leibinger Family of Neurosurgical Products, (1993) 1.

Leibinger et al., "The ZD Stereotactic System", Leibinger et al. v. McCrory et al., Interference No. 103,657 (1992), 19.

Leibinger, "Summary of Safety and Effectiveness", Marker System for Stereotaxic Navigation, (Mar. 1995), pp. 38-46.

Leibinger, et al., "The F.L. Fischer™ Stereotactic Products by Leibinger™", Leibinger et al. v. McCrory et al., Interference No. 103,657, (1993), 1.

Motti, E. D. et al., "Head-holder Interfacing Computed Tomography with Talairach Stereotactic Frame", Journal of Neurosurgical Sciences, 27(3), (1983), 219-223.

Office Action in U.S. Appl. No. 10/374,677 by James Kish, mailed Sep. 5, 2007.

Rousseau et al., "Validation of a New Method for Stereotactic Localization using MR Imaging", Journal of Computer Assisted Tomography, (1991) 291-296.

Rousseau, J. et al., "A frameless method for 3D MRI and CTstereotaxic localisation", European Radiology, (1992), pp. 1286-1292.

Waltregny et al., "Application of the Talairach stereotaxic system for the purpose of estalishing a common reference plane for brain imaging techniques (CAT scan, NMRI, PET scan)", Revue d'Electroencephalographic et de Neuro-physiologie Clinique, 16(3), (1986), 269-271.

* cited by examiner

FIDUCIAL MARKER DEVICES, TOOLS, AND METHODS

FIELD OF THE INVENTION

This document relates generally to imaging and/or locating a subject, such as for performing surgical intervention, and more specifically, but not by way of limitation, to fiducial marker devices and associated tools and methods.

BACKGROUND

Fiducial markers that can be located and recognized by an imaging system or other system are useful in neurosurgery and other applications. Examples of imaging system modalities include, among other things, magnetic resonance imaging (MRI), computed tomography (CT), positron emission tomography (PET), and single photon emission computed tomography (SPECT).

For example, in one technique, multiple fiducial markers are screwed into the patient's skull to define landmarks recognizable by an imaging system. The imaging system is used to obtain one or more preoperative images of the patient's brain. Recognizable images of the fiducial markers appear on such preoperative images. Such a bone-anchored fiducial marker typically includes an externally threaded bone-screw portion, which is driven into the skull. A threaded shaft rises up and out of the skull from the bone-screw. The threaded shaft typically receives a screwed-on imagable sphere that is visible on an MRI or CT image. The multiple fiducial markers on the patient's skull define landmarks on preoperative images that are useful to the physician for planning entry coordinates on the patient's skull and for planning a trajectory to a target location in the brain. An image-guided surgical workstation uses these preoperative images and the planning data to guide the neurosurgeon while actually performing the subsequent surgical procedure.

After the preoperative planning phase, the patient is brought into the operating room so that the planned surgical procedure can be performed. On the operating table, the patient's skull is clamped in a head-frame or otherwise immobilized. In order to use the preoperative images provided by the image-guided workstation to guide the surgeon during the surgical procedure, the patient's skull must first be "registered" to the preoperative images. The registration creates an association between (1) the actual physical location of the fiducial markers on the patient's skull in the operating room and (2) the locations of the images of the fiducial markers visible on the preoperatively-obtained images. This allows mapping between the actual space in which the patient is located to the space defined by the preoperative images.

According to one registration technique, a "wand" is used to perform this patient registration. The wand typically includes multiple light-emitting diode (LED) locators or reflective locators, which are visible to an infrared camera or other detector of an optical positioning system in the operating room. The camera and optical positioning system are operatively connected to the image-guided workstation. The locators define the position of the wand in the operating room, including the position of a sharp tip portion of the wand, which is in a known physical relationship to the locators. To register the patient, the imagable spheres are unscrewed from the fiducial marker shafts, and replaced by respective "divots" that are sized and shaped to receive the wand tip. These divots are screwed onto the respective fiducial marker shafts, such that when the wand tip is received into the maximum depression point of the divot, the wand tip then corresponds to the same location as the center of the imagable sphere when the imagable sphere was screwed onto the fiducial marker shaft. A reference divot is typically also present in the operating room at a known location, such as attached to the operating table or the patient's skull-immobilizing head-frame. During the patient registration process, the surgeon touches the wand tip to the reference divot (to provide an absolute positional reference to the image-guided workstation), and then to each fiducial marker divot. This permits the image-guided workstation to correlate the actual physical location of the patient's skull to the preoperative images. The physician can then use the wand, in conjunction with the preoperative images provided by the image-guided workstation, to locate an appropriate entry point and trajectory to the target in the brain.

The present inventors have recognized that problems with the above registration procedure include patient discomfort caused by the presence of the fiducial markers, increased trauma to the patient resulting from using multiple fiducial markers screwed into different locations of the patient's skull, the difficulty of unscrewing the imaging spheres and replacing them with the registration divots, a limited field of view of the camera used in the operating room, and the difficulty of constructing a multi-modal fiducial marker that can be recognized by more than one imaging modality or positioning system. Moreover, the present inventors have recognized the desirability of streamlining the registration process to reduce its time and cost. For these and other reasons, which will become apparent upon reading the following detailed description and viewing the drawings that form a part thereof, the present inventors have recognized an unmet need for improved fiducial marker devices, tools, and methods.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

FIG. 1A is a schematic diagram illustrating generally one example of an imagable fiducial marker that includes a built-in conical divot or other male or female receptacle, or the like.

FIG. 2A is a schematic diagram illustrating generally an alternative example of a fiducial marker that includes a cylindrical imaging fiducial locator and a conical or other divot or other receptacle for receiving a positioning wand tip or the like.

FIG. 6A is a schematic diagram illustrating generally a divot assembly that includes a swiveling tilted head carrying a conical or other divot or the like.

DETAILED DESCRIPTION

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the scope of the present invention. The following detailed description is, therefore, not to be taken in a limiting sense, and the scope of the present invention is defined by the appended claims and their equivalents.

In this document, the terms "a" or "an" are used, as is common in patent documents, to include one or more than one. Furthermore, all publications, patents, and patent documents referred to in this document are incorporated by reference herein in their entirety, as though individually incorporated by reference. In the event of inconsistent usages between this documents and those documents so incorporated by reference, the usage in the incorporated reference(s) should be considered supplementary to that of this document; for irreconcilable inconsistencies, the usage in this document controls.

In this document, the term "assembly" is not intended to be limited to a structure that is assembled from multiple components, but also includes unitary or integrally-formed structures or the like.

Example 1

Figure 1A:
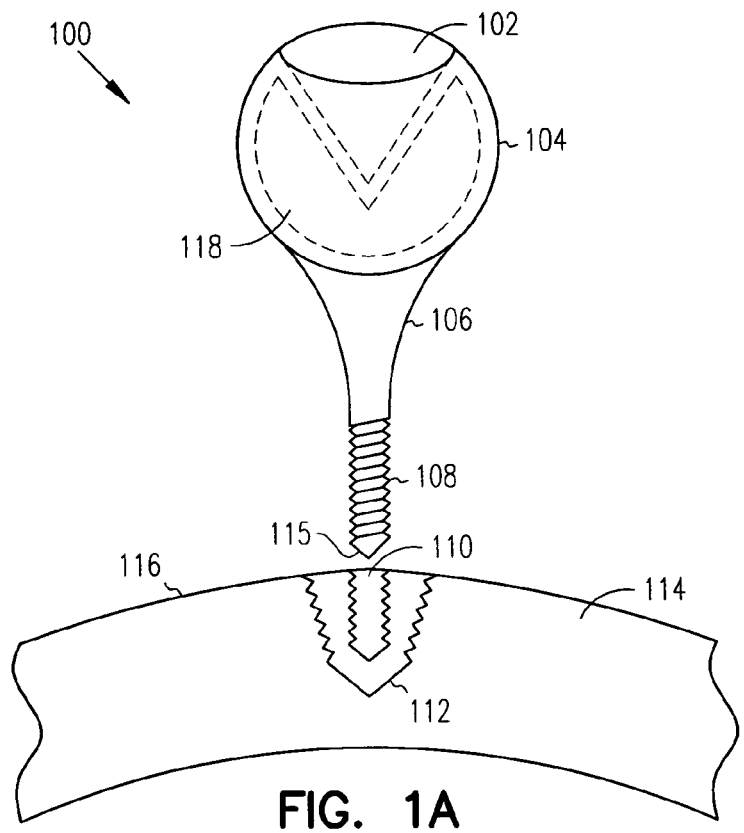

FIG. 1A is a schematic diagram illustrating generally, by way of example, but not by way of limitation, one example of an imagable fiducial marker 100 that includes a built-in divot 102. In this example, the divot 102 includes a female receptacle, such as the illustrated conical depression. However, as used herein, a divot also refers to any other male or female receptacle, or the like. The divot 102 is capable of receiving a correspondingly sized and shaped mating tip of a positioning wand or like instrument. Such a wand or instrument is useful for registering the actual physical location of the patient's skull to preoperative or other images of the subject's brain. Such images are typically stored in a memory of an image-guided surgical (IGS) computer workstation.

In the example illustrated in FIG. 1A, the fiducial marker 100 includes an imagable substantially spherical fiducial locator 104. The fiducial 104 is locatable using one or more imaging system modalities. In this example, a shaft 106 extends orthogonally outward from a circumferential portion of the spherical fiducial 104. The shaft 106 includes an externally threaded portion 108. The externally threaded portion 108 is sized and shaped for being received within a correspondingly sized and shaped mating internally threaded receptacle 110 of an externally-threaded self-tapping base 112. In this example, the base 112 is capable of being mounted in a skull 114, such as either flush to (or even recessed from) an outer surface 116 of the skull 114. One example of a suitable base 112 is described in commonly-assigned Mazzocchi et al. U.S. patent application Ser. No. 10/206,884 entitled FIDUCIAL MARKER DEVICES, TOOLS, AND METHODS, which was filed on Jul. 24, 2002, and which is incorporated herein by reference in its entirety, including its disclosure relating to a flush or recessed mounted base and other fiducial marker devices, tools and methods. However, in alternative examples, the base 112 need not be configured for mounting flush to or recessed from the outer surface 116 of the skull 114. In this example, the shaft 106 includes a pointed tip 115. This permits the shaft 106 to more easily penetrate a sterile drape that, in certain circumstances, may be placed over the patient's skull 114. Moreover, in this example, the receptacle 110 of the base 112 is shaped to accommodate the pointed tip 115. However, in an alternative example, the tip 115 need not be pointed.

In one example, the imaging spherical fiducial locator 104 houses a generally spherical (e.g., except for the conic cut-away of the divot 102) sealed interior cavity 118. In one example, the cavity 118 is filled with an imagable fluid that is visible on one or more imaging modalities (e.g., MR, CT, etc.). In this example, the apex of the conic divot 102 is located at a center of mass of the imaging spherical fiducial locator 104. This allows the tip of a positioning wand (recognizable by a camera in an optical position locating system that is coupled to the image-guided surgical workstation) to be inserted into the divot 102. This results in the wand tip being located at the center of mass of the imaging spherical fiducial locator 104. This is useful for assisting in registering the physical location of the patient to the preoperative images stored in the image-guided surgical workstation.

Unlike fiducial marker assemblies that require the user to attach an imaging fiducial while obtaining the preoperative images of the patient's brain, and to then replace that imaging fiducial with a separate divot during patient registration in the operating room, the fiducial marker 100 illustrated in FIG. 1A does not require any such exchange of the imaging fiducial for a separate divot. Instead, the divot is integrated into the imaging fiducial itself, as illustrated in FIG. 1A. This reduces the complexity of the image-guided surgical procedure and, therefore, reduces its cost.

In one example (but not by way of limitation), the base 112 is constructed of stainless steel. The shaft 106 and the imaging spherical fiducial locator 104 are constructed of molded plastic polymer. In this example, the imaging spherical fiducial locator 104 includes an open cavity 118 for receiving the imaging fluid, and for then receiving an insertable plastic conical divot 102 that adhesively or otherwise seals the cavity 118 to retain the imaging fluid therein. The imaging fluid in the cavity 118 is visible and provides good contrast on images produced by at least one imaging modality. In one example, the imaging fluid is multimodal (i.e., locatable by more than one imaging modality), such as by using a mixture of different imaging fluids that are locatable on different imaging modalities. In an alternative example, the plastic forming the imaging spherical fiducial locator 104 includes a substance that is viewable on a first imaging modality, while the imaging fluid within the cavity 118 is viewable on a different second imaging modality.

In one such illustrative example, the plastic imaging fiducial locator 104 is doped with a substance having a high atomic number (Z), such as barium, titanium, iodine, silver, gold, platinum, iodine, stainless steel, titanium dioxide, etc. that provide good contrast on a CT or other radiographic imaging system. In this illustrative example, the fluid within the cavity 118 includes gadopentatate dimeglumine, gadoteridol, ferric chloride, copper sulfate, or any other suitable MRI contrast agent, such as described in chapter 14 of Magnetic Resonance Imaging, $2^{nd}$ ed., edited by Stark and Bradley, 1992, which is incorporated herein by reference.

In an alternative multimodal example, the cavity 118 is omitted. Instead, the spherical fiducial locator 104 is constructed of a substantially solid plastic or other material that is hygroscopic, that is, capable of receiving and retaining a fluid, such as an imaging fluid that is viewable on an imaging system (e.g., an MRI imaging system or the like). In a further example, the plastic forming the spherical fiducial locator 104 is doped or otherwise includes a substance that is viewable on a different imaging system, such as, for example, a CT or other radiographic imaging system. Illustrative examples of solid plastics that can be made hygroscopic include, among other things, nylon and polyurethane. Using a hygroscopic material avoids the complexity and cost associated with manufacturing a sealed cavity 118 for retaining an imaging fluid. Moreover, by adapting the solid hygroscopic plastic for imaging using a first modality, and by using the imaging fluid for imaging using a second modality, each of the solid and the fluid can be separately tailored toward providing better contrast for its particular imaging modality.

In another alternative example in which the cavity 118 is omitted, the fiducial locator 104 includes a rigid solid (e.g., substantially spherical, but for the conic divot) interior. This solid material is doped with a substance that provides good contrast using a first imaging modality (e.g., CT). A hygroscopic outer coating is formed thereupon. The coating permits soaking up a fluid that provides a good contrast using a second imaging modality (e.g., MRI).

In a further example of the fiducial marker 100 illustrated in FIG. 1A, the outer surface of the imaging spherical fiducial locator 104 is reflective of light or other electromagnetic energy. Consequently, it is also locatable by the operating room camera in an optical positioning system that is coupled to the image-guided workstation (e.g., during patient registration). In one such example, the outer surface of the imaging spherical fiducial locator 104 includes light-reflective microspheres (e.g., embedded in an adhesive covering the imaging spherical fiducial 104). In another such example, the outer surface of the imaging spherical fiducial 104 is covered with an adhesive-backed light-reflective tape, such as SCOTCHLITE® 9810 Reflective Material Multipurpose Tape sold by Minnesota Mining and Manufacturing Co. ("3M®"), of Saint Paul, Minn.

Figure 2A:
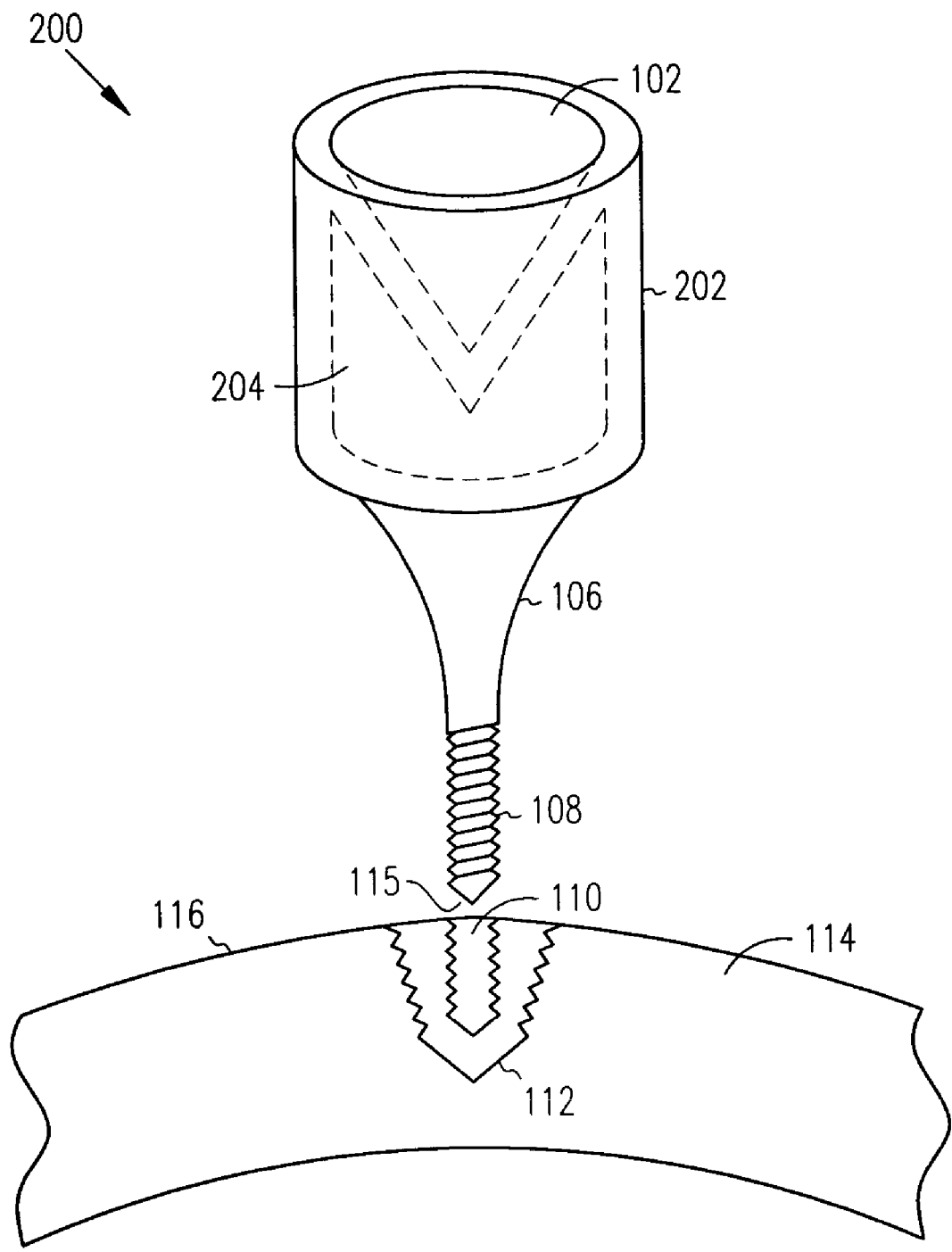

FIG. 2A is a schematic diagram illustrating generally, by way of example, but not by way of limitation, an alternative example of a fiducial marker 200 that includes a generally cylindrical imaging fiducial locator 202 and a conical or other divot 102. In one example, the generally cylindrical imaging fiducial locator 202 includes a sealed cavity 204 for receiving and retaining an imagable fluid, as discussed above. In another example, the sealed cavity 204 is omitted, as discussed above. In one such example, the generally cylindrical imaging fiducial locator 202 is instead constructed of a substantially solid hygroscopic plastic that carries an imagable fluid (as discussed above), such as for providing multimodal contrast across different imaging modalities. In a further example, the generally cylindrical outer surface of the imaging fiducial locator 202 is reflective, as discussed above, such that the imaging fiducial locator 202 is also visible to a camera of an optical position locating system that is coupled to an image-guided surgical workstation (e.g., during patient registration and/or a subsequent image-guided surgical procedure). In one such example, the imaging fiducial locator 202 is covered with adhesive-backed reflective tape taken from a rectangular strip of such tape that is wound into a roll. In this example, the generally cylindrical shape of the outer surface of the imaging fiducial locator 202 is much easier to wrap using a wound rectangular strip of the adhesive reflective tape than a spherical surface, such as is illustrated in FIG. 1A, and therefore costs less to manufacture. In this document, the term "generally cylindrical" is not limited to a perfectly cylindrical surface, but instead is understood to include any faceted or other column or like structure (e.g., an octogonal cylinder a hexagonal cylinder, etc.) that includes a lateral peripheral surface that easily accommodates receiving a wound rectangular or similar strip of tape (as opposed to a spherical, elliptical, or conical surface, to which is more difficult to evenly apply a wound rectangular strip of tape taken from a roll). Examples of such generally "cylindrical" columnar structures having faceted lateral peripheral surfaces are illustrated in FIG. 3C.

Figure 1B:
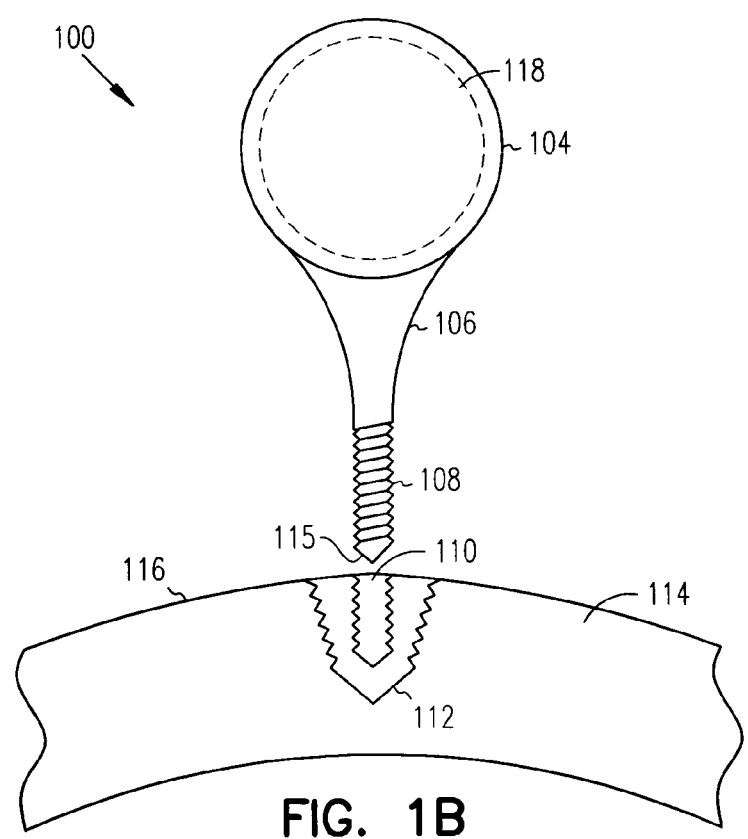
FIG. 1B is a schematic diagram illustrating generally one example of an imagable fiducial marker that omits the divot illustrated in FIG. 1A, but which is both locatable by a remote positioning system and imagable by one or more imaging modalities.
Figure 2B:
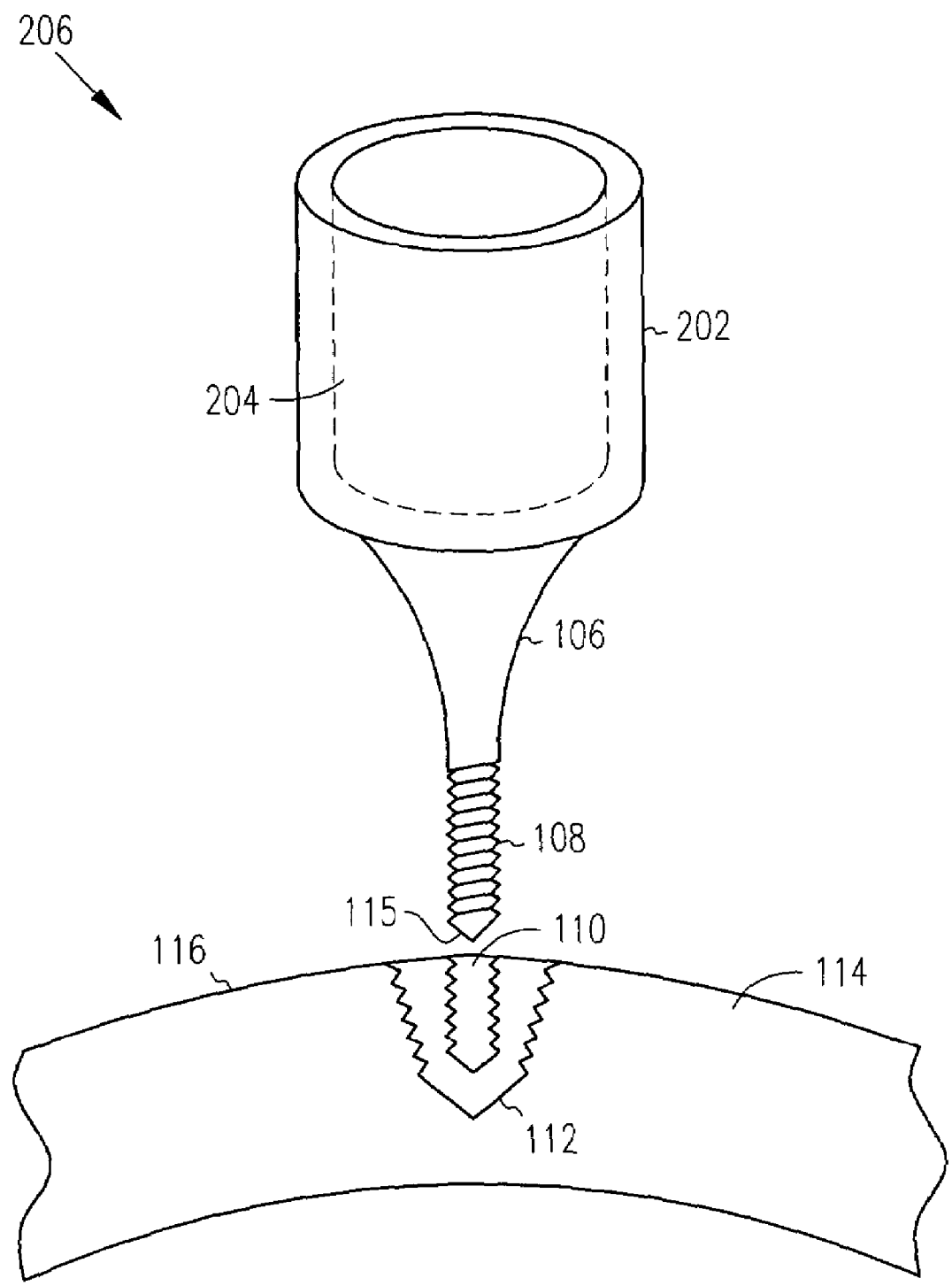
FIG. 2B is a schematic diagram illustrating generally one example of an imagable fiducial marker that omits the divot illustrated in FIG. 2A, but which is both locatable by a remote positioning system and imagable by one or more imaging modalities.

In an alternate example to the illustrations of FIGS. 1A and 2A, the divot 102 is omitted from the fiducial marker 100 or 200. However, the resulting fiducial marker is still configured to be locatable by a remote positioning system as well as imagable using one or more imaging modalities. In one such example, the outer surface 104 or 202 is still configured to be light reflective, such as discussed above. In one such example, the fiducial markers 100 and 200 still advantageously are locatable using one or more imaging modalities (e.g., MR, CT, or other imaging system providing 3D or other internal images within a subject) as well as also being locatable external to the subject, such as by using a remote camera or like component of an optical or other positioning system, e.g., that is coupled to an image-guided workstation. In one example, this permits automatic registration of the actual location of the subject in the operating room (e.g., using the cameras to locate the light reflective fiducial markers 100 or 200) to preoperative images of the patient on which the same imagable fiducial markers 100 and 200 appear. This eliminates any need to register the patient by inserting an optically-locatable positioning wand tip into a divot of each fiducial marker (and also eliminates any need for a reference divot or other absolute position reference), because the fiducial markers themselves are optically locatable and registerable to known locations on the preoperative images. Therefore, in this example, the divots 102 are not needed and can be omitted, as illustrated by the divotless spherical imagable reflective fiducial marker 120 in FIG. 1B and the divotless cylindrical imagable reflective fiducial marker 206 in FIG. 2B. Although FIG. 2B illustrates an example including a cavity 204 for carrying a liquid contrast agent, in an alternative example, the cavity 204 is omitted, and the fiducial marker 206 includes a solid structure that is doped or otherwise configured (e.g., hygroscopic) for providing good imaging contrast using one (e.g., CT) or more imaging modalities.

In yet another example, the fiducial markers 100 and 200 respectively illustrated in FIGS. 1A and 2A include the illustrated divots 102 and are locatable by a remote positioning system (such as by including light-reflective outer surfaces and/or embedded coils that perform magnetic field sensing in a magnetic field based positioning system). However, in this example, the fiducial markers 100 and 200 need not be configured for providing contrast on the one or more imaging modalities. In such an example, the preoperative images are taken with imagable fiducial markers placed within respective bases 112. Such imagable fiducial markers are then replaced (within their respective bases 112) by nonimagable fiducial markers that are locatable by a remote positioning system, such as by including both a divot and a light-reflective surface. The light reflective surface permits automatic location by the remote positioning system. However, if the reflective surface is dirty or otherwise unrecognizable by the remote positioning system, a wand or other locating instrument can be placed within the divot to perform the remote locating of the fiducial marker.

Moreover, although FIGS. 1A and 2A illustrate examples in which a shaft 106 is received within a base 112 that is mounted flush to (or recessed from) the outer surface 116 of the skull 114, this is not required. In one alternate example, the shaft 106 is manufactured as a stainless steel or other suitable material that is capable of acting as a self-tapping bone screw. In such an example, the threaded portion 108 of the shaft 106 is threaded directly into the skull 114 without using any base 112. In another alternate example, the base 112 includes a shaft or flange portion that rises above the outer surface 116 of the skull 114. In certain examples, the fiducial markers 100 and 200 may use a threaded or other shaft 106 for coupling to the base 112, or alternatively may use a snap-fit clip or a like attachment device for coupling to the base 112.

Figure 3A:
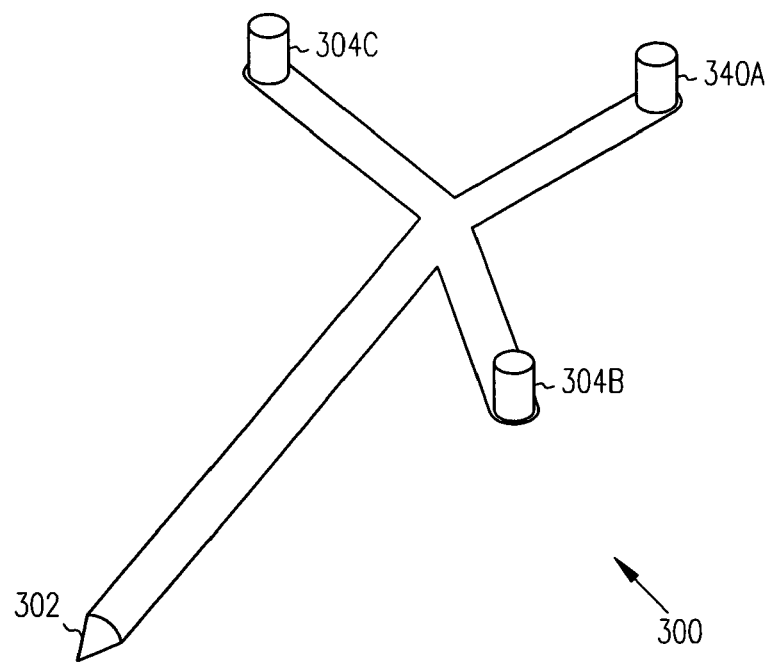
FIG. 3A is a schematic diagram illustrating generally one example of a positioning wand for use in conjunction with a remotely-located camera or other like device of an optical positioning system, such as can be coupled to an image-guided surgical workstation in an operating room.

FIG. 3A is a schematic diagram illustrating generally, by way of example, but not by way of limitation, one example of a positioning wand 300, such as for use with a remotely-located camera or other like device of an optical positioning system configured for being coupled to an image-guided surgical workstation in an operating room. In this example, the wand 300 includes a tip 302 that is sized and shaped to permit being received in a divot 102 of a skull-mounted fiducial marker (such as fiducial markers 100 and 200). The wand 300 includes a plurality of cylindrically-shaped fiducial locators 304 that are locatable by the camera or other like device of the optical positioning system. The fiducial locators 304 (which typically need not include divots) on the wand 300 are positioned in a known spatial relationship to each other and to the tip 302 of the wand 300. By recognizing the locations of the fiducial locators 304, the optical positioning system is capable of computing the location of the wand tip 302, which is in a known spatial relationship with the configuration of fiducial locators 304. This permits the wand 300 to be used in conjunction with the optical positioning system to register the patient and to further plan and/or perform the surgical procedure using the image-guided surgical workstation. The fiducial locators 304 are covered with adhesive-backed reflective tape, as discussed above. The cylindrical (or faceted cylindrical) shape of the fiducial locators 304 permits easier wrapping by the reflective tape than the spherical fiducials, as discussed above. This reduces the cost of manufacturing the fiducial locators 304 and, in turn, reduces the cost of manufacturing the positioning wand 300.

Figure 3B:
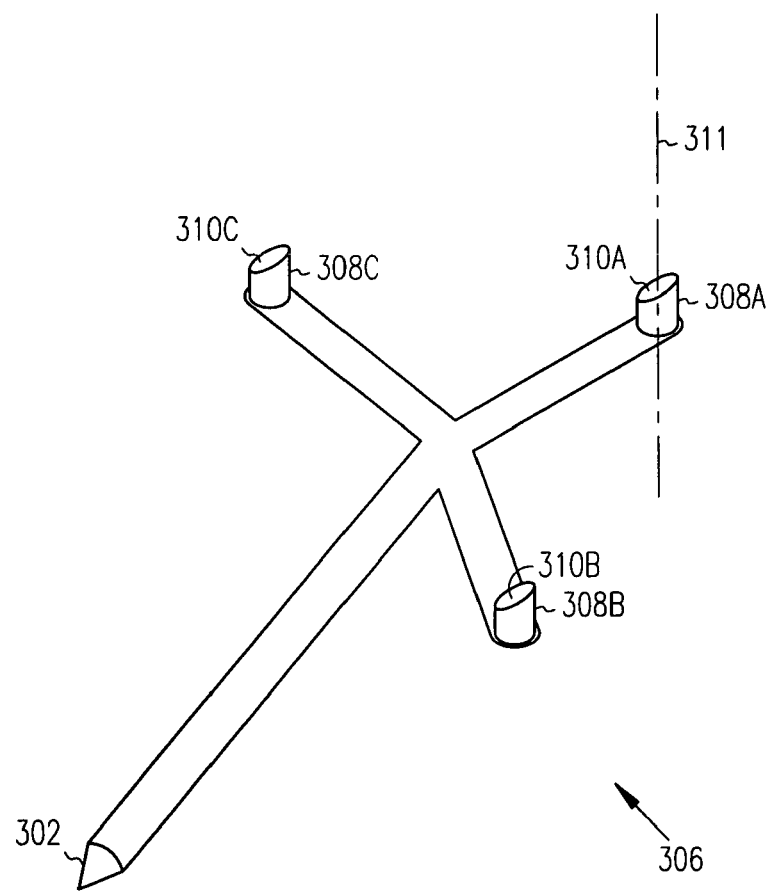
FIG. 3B is a schematic diagram, similar in certain respects to FIG. 3A, illustrating generally one example of a positioning wand including energy reflective surfaces that are capable of being oriented or aimed toward a remote detector.
Figure 3C:
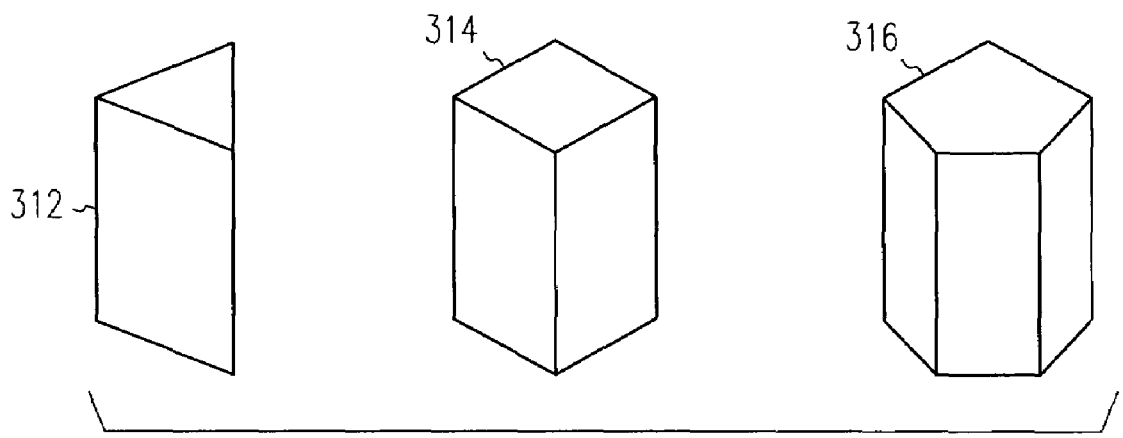
FIG. 3C is a perspective view schematic diagram illustrating generally, by way of example, but not by way of limitation, certain generally "cylindrical" columnar structures having faceted lateral peripheral surfaces.

FIG. 3B is a schematic diagram, similar in certain respects to FIG. 3A, but illustrating a wand 306 that includes locators 308A-C having swiveling or fixed cylindrical locators 308A-C having respective slanted (e.g., flat, parabolic, or other) top surfaces 310A-C (e.g., non-orthogonal with respect to a longitudinal center axis 311 of the locator 308) that reflect light or other electromagnetic energy for being located by a remote detector. In an example in which the locators 308A-C swivel, each such locator 308 includes a shaft inserted into a hole or other receptacle in the wand 306. This permits the locator 308 to rotate with respect to its mounting location on the wand 306. Either the wand 306 itself or the individual locators 308A-C are oriented by the user to aim the reflective surfaces 310A-C toward a camera or other detector of an optical positioning system. In one further example, the circumferential surfaces of the cylindrical locators 308A-C are also light-reflective, however, this is not required. In one such cost-effective example, the reflective tape disks are adhered to the flat slanted top surfaces 310A-C and the circumferential lateral surfaces of the cylindrical locators 308A-C are not reflective.

FIG. 3C is a perspective view schematic diagram illustrating generally, by way of example, but not by way of limitation, certain generally "cylindrical" columnar structures 312, 314, and 316 having faceted lateral peripheral surfaces. Such surfaces are conducive to receiving a rectangular or like strip of adhesive reflective tape. Such structures, therefore, are particularly well-suited for implementing locators that are remotely locatable by an optical positioning system. Such remotely detectable locators are suitable for use in the fiducial markers illustrated in FIGS. 2A and 2B, as well as for use in the remotely detectable locators of the positioning wands illustrated in FIGS. 3A and 3B. Such remotely detectable locators are also useful for being affixed in a known relationship to the patient, such as to the operating table or to a skull-immobilizing headframe. This provides a remotely detectable absolute positional reference to an optical positioning system. Such remotely detectable locators are also useful for being affixed to a biopsy needle, shunt catheter, or other instrument being introduced through a trajectory guide device or otherwise used in an image-guided surgical procedure.

Figure 3D:
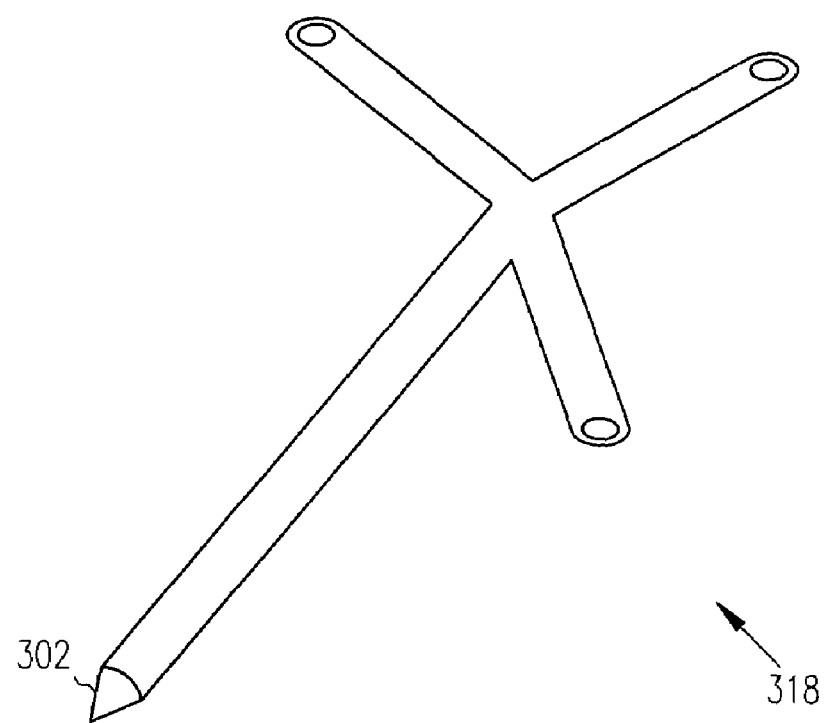
FIG. 3D is a schematic diagram illustrating generally an example of a positioning wand with flat disk-shaped pieces of reflective tape are attached in a known configuration.

FIG. 3D is a schematic diagram illustrating generally, by way of example, but not by way of limitation, an alternative example of a positioning wand 318. In this example, which flat disk-shaped pieces of reflective tape are attached to the wand 318 in a known configuration, such as at the distal ends of radial arms extending therefrom.

Example 2

Figure 4:
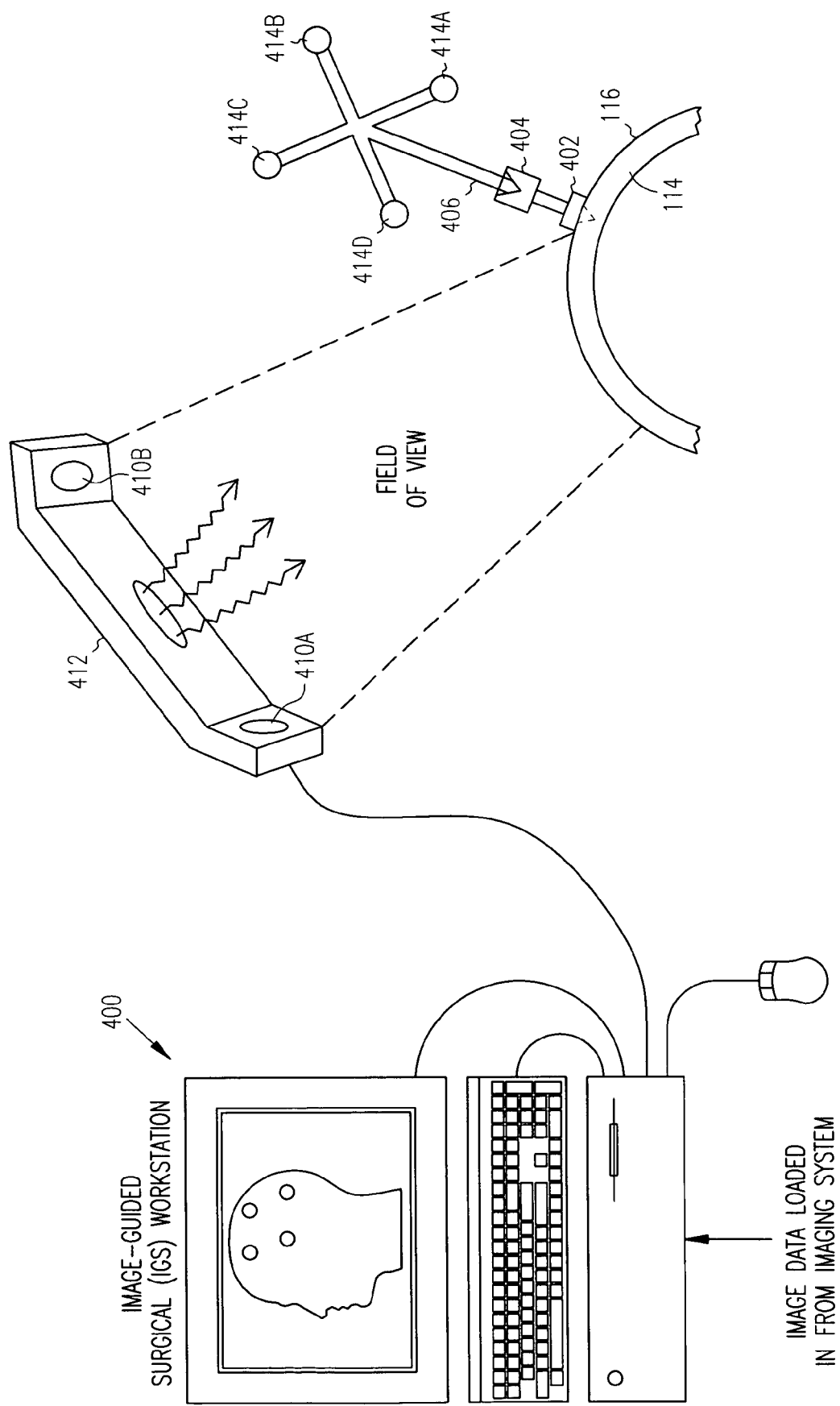
FIG. 4 is a schematic diagram illustrating generally, by way of example, but not by way of limitation, an image guided surgical (IGS) computer workstation to which an optical positioning system is coupled.

FIG. 4 is a schematic diagram illustrating generally, by way of example, but not by way of limitation, an image guided surgical (IGS) computer workstation 400, which is capable of displaying previously acquired and loaded preoperative images of a patient's skull. On these preoperative images appear viewable images of imagable fiducial markers that were screwed into the patient's skull before the preoperative imaging (e.g., using MRI, CT, etc.). In the example illustrated in FIG. 4, the imagable fiducial locators have been unscrewed from respective bases 402 screwed into the patient's skull. The imagable fiducial locators have been replaced by patient registration divot assemblies 404 that have been screwed into (or otherwise coupled to) respective bases 402 in the patient's skull 114. In this example, the registration divot assemblies 404 are configured to receive a shaft tip 406 of a positioning wand 408 that is locatable by one or more remote cameras 410A-B (or other sensing devices) of an optical position detection system 412 connected to the IGS workstation 400. In one example, the positioning wand 408 includes spherical reflective fiducial locators 414. The fiducial locators 414 are arranged in a known spatial relationship to each other (however, it may alternatively use other reflective locators such as discussed elsewhere in this document). The optical positioning system 412 includes an infrared light (or other energy source) 416 that provides light that is reflected from the reflective fiducial locators 414. This permits the reflective fiducial locators 414 on the positioning wand 408 to be located and recognized by the cameras 410A-B. In some circumstances, however, the field of view (or "sweet spot" of the field of view) provided by cameras 410A-B is limited. This sometimes makes it difficult for the optical positioning system 412 to recognize the positioning wand 408. Moreover, the recessed receptacle in the divot assembly 404 typically limits the range within which the probe 408 can be manipulated (e.g., to bring it within the field of view) while retaining the wand tip 406 within the recessed receptacle.

Figure 5:
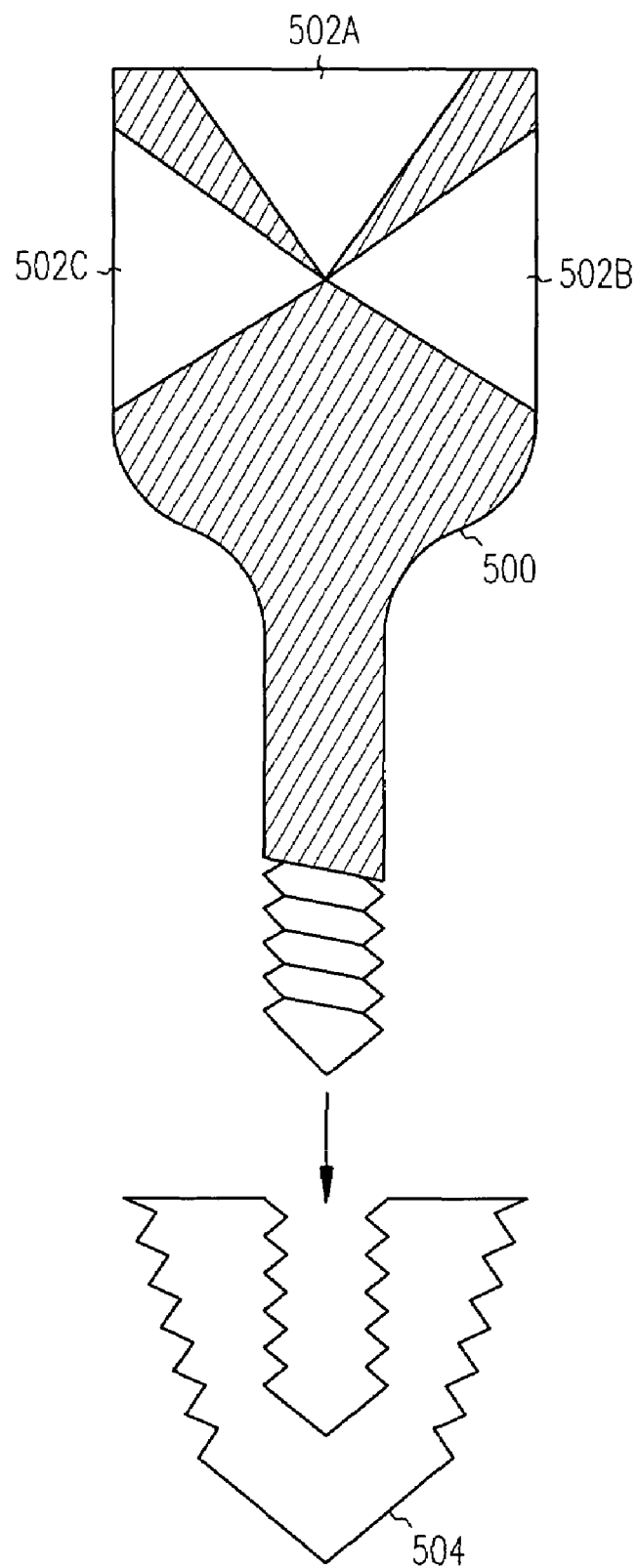
FIG. 5 is a schematic diagram illustrating generally a unitary divot assembly that includes multiple divots.

FIG. 5 is a schematic diagram illustrating generally, by way of example, but not by way of limitation, a unitary divot assembly 500 that includes multiple divots 502. In this example, the unitary divot assembly 500 is configured such that it can be threaded into or otherwise coupled to a base 504 that is secured to the patient's anatomy (wherein the base 504 is also configured for alternatively receiving an imagable fiducial locator, e.g., during preoperative imaging). FIG. 5 illustrates multiple conical receptacle divots 502 having commonly located apexes. These commonly located apexes are designed to coincide with the center of the image produced by the imagable fiducial locator for which the divot assembly 500 has been substituted during patient registration. In the illustrated example, the divots include a top conical divot 502A and four side conical divots 502B-F. The four side conical divots 502B-F are distributed around the cylindrical lateral peripheral circumference of the upper portion of the divot assembly 500. The wand tip 406 may be inserted into any one of the divots 502. This permits a greater range of motion of the positioning wand 408. As a result, it is easier to bring the reflective fiducials 414 on the positioning wand 408 into the field of view of the cameras 410A-B of the optical positioning system 412.

Figure 6A:
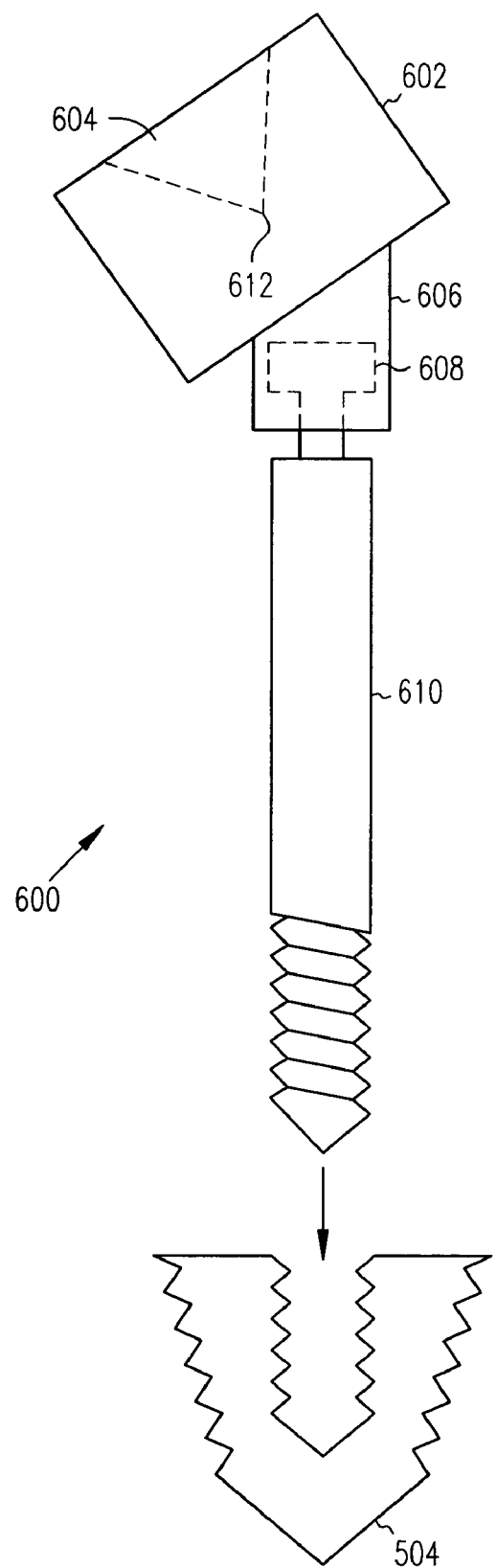

FIG. 6A is a schematic diagram illustrating generally, by way of example, but not by way of limitation, a divot assembly 600 that includes a swiveling tilted head 602 carrying a conical or other divot 604 or the like. In this example, the head 602 is tilted with respect to a cylindrical coupling 606 extending outwardly therefrom. The coupling 606 includes a hollow interior or other (female or male) connector that snap-fits onto and rotatably rides upon a mating (male or female) connector 608 that is located at a proximal end of a shaft 610 portion of the divot assembly 600. The swiveling apex 612 of the divot 604 is designed to coincide with the center of mass of the imagable fiducial locator for which the divot assembly 600 has been substituted during patient registration. The swiveling-tilted head 602 permits a wide range of motion of the positioning wand 408 when the wand tip 406 is inserted into the divot 604. As a result of such rotational articulation, it is easier to bring the reflective fiducial locators 414 on the positioning wand 408 into the limited field of view of the cameras 410A-B of the optical positioning system 412.

Figure 7A:
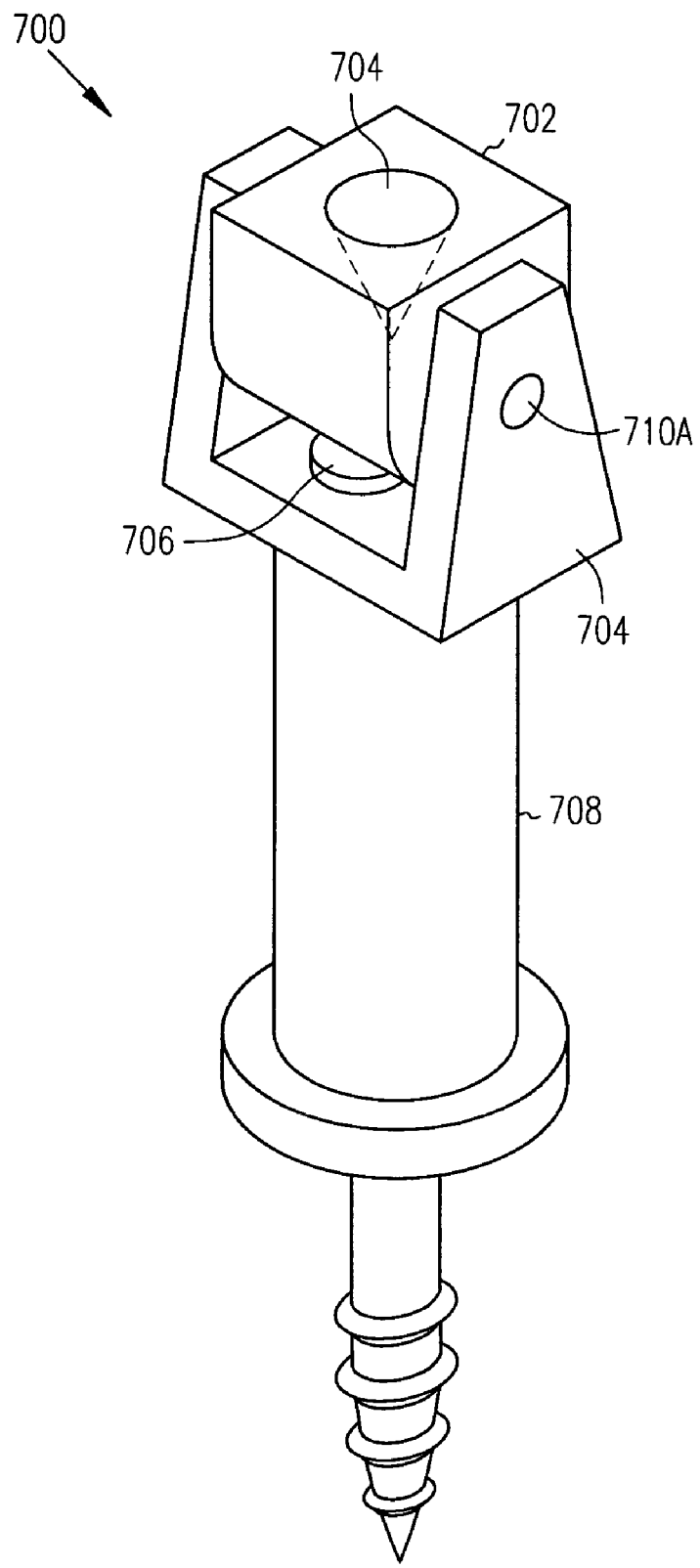
FIG. 7A is a schematic diagram illustrating generally a divot assembly that includes a swiveling and pivotable head carrying a conical or other divot.

FIG. 7A is a schematic diagram illustrating generally, by way of example, but not by way of limitation, a divot assembly 700 that includes a swiveling and pivotable head 702 carrying a conical or other divot 704. In this example, the head 702 is carried by a shackle-like U-shaped bracket 704 that rotatably rides upon a snap-fit or other capturing post 706 that extends upward from a shaft portion 708 of the divot assembly 700. This allows swiveling of the bracket 704 (and the head 702 carried by the bracket 702) with respect to the shaft 708. In this example, the head 702 is suspended between upward-projecting risers of the bracket 704 by axels 710A-B extending outward from opposing sides of the head 702 and received within corresponding receptacles in the risers of the bracket 704. This permits pivoting/tilting articulation of the head 702 with respect to the swiveling bracket 704. Therefore, this example provides a swiveling and adjustably tiltable divot 704 that is designed such that its apex 712 coincides with the center of mass of the imagable fiducial locator for which the divot assembly 700 has been substituted during patient registration. Among other things, the swiveling tiltable head 702 advantageously permits a greater range of motion of the positioning wand 408 when the wand tip 406 is inserted into the divot 704. As a result, it is easier to bring the reflective fiducials 414 on the positioning wand 408 into the limited field of view of the cameras 410A-B of the optical positioning system 412.

Figure 6B:
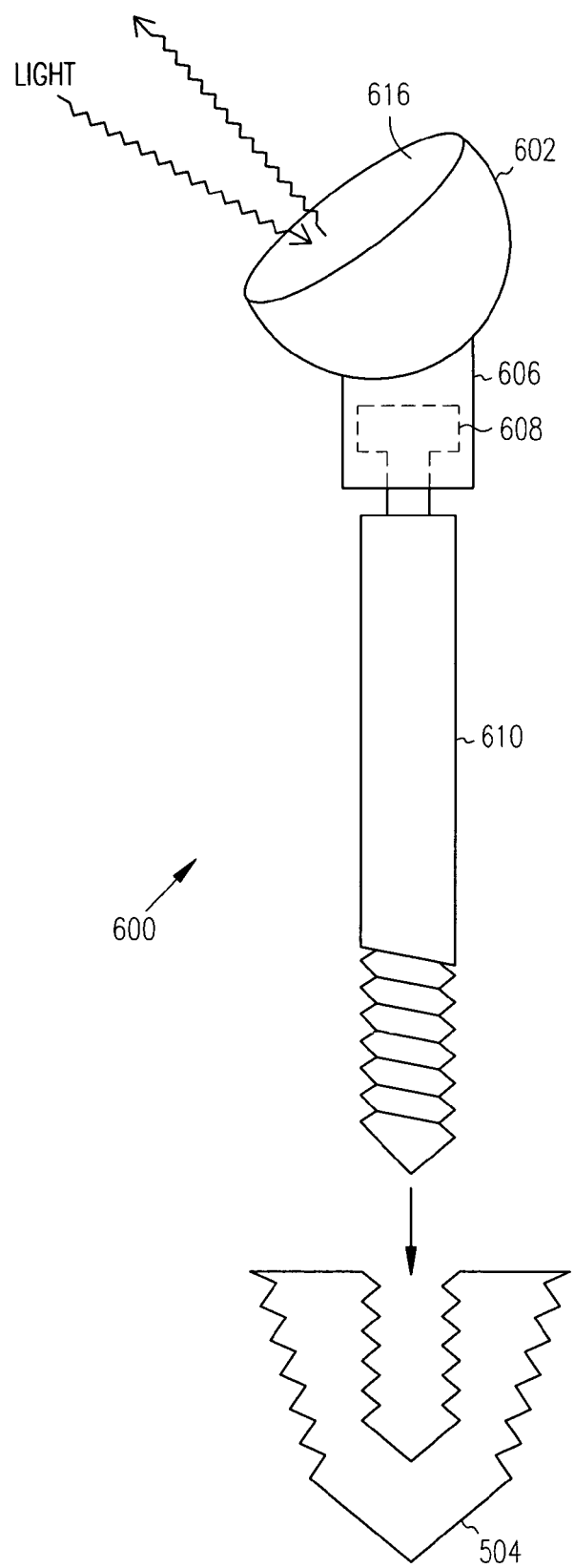
FIG. 6B is a schematic diagram illustrating generally a locator assembly that includes a swiveling tilted head including a surface that reflects electromagnetic energy.
Figure 7B:
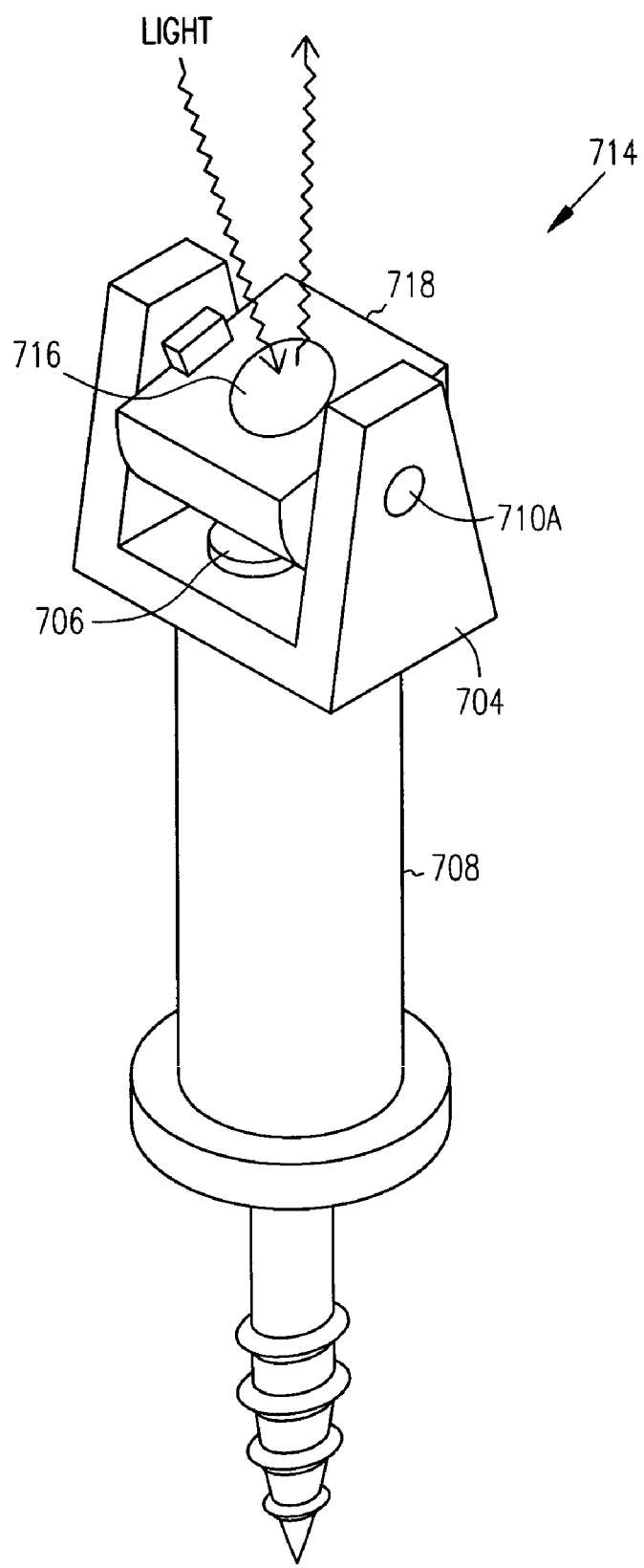
FIG. 7B is a schematic diagram illustrating generally a divot assembly that includes a swiveling and pivotable head including a surface that reflects electromagnetic energy.

FIGS. 6B and 7B are schematic diagrams that are similar in certain respects to FIGS. 6A and 7A. However, the locator assemblies 614 and 714 illustrated by respective FIGS. 6B and 7B omit the respective divots 604 and 704. Instead, the locator assemblies 614 and 714 provide aimable electromagnetic energy (e.g., light) reflective surfaces 616 and 716, respectively. The reflective surfaces 616 and 716 are aimed at the camera of an optical positioning system 412 to allow automatic detection of the locator assemblies 614 and 714 without requiring the use of a positioning wand 408.

The reflective surfaces 616 and 716 are configured so that, when aimed properly, they produce a reflected image that can be correlated to a previously acquired patient image on which an image of an imagable fiducial marker appears. In one such example, reflective surface 616 corresponds to the center of mass of a similarly sized spherical locator on an imagable fiducial marker assembly for which locator assembly 614 is substituted during patient registration. In another such example, reflective surface 716 includes a circular disk-shaped piece of reflective tape affixed to a surface 718 such that this reflective disk pivots about the axis provided by axels 710A-B. In this manner, the reflected disk shape corresponds to the center of mass of a similarly sized spherical locator on an imagable fiducial marker assembly for which locator assembly 714 is substituted during patient registration.

Example 3

Figure 8:
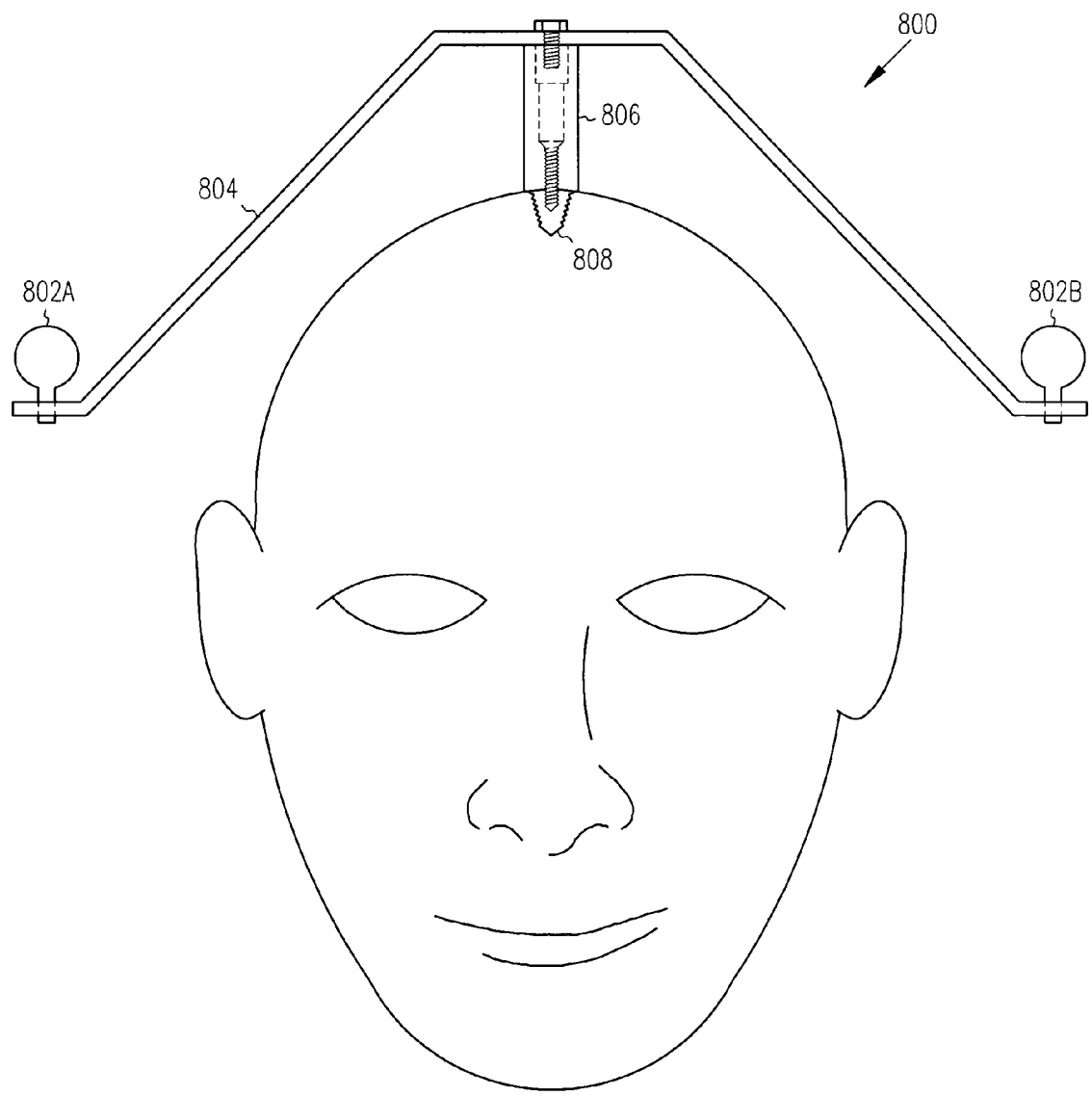
FIG. 8 is a schematic diagram illustrating conceptually a fiducial marker carrier that is attachable to (and also detachable from) a single location on the patient's skull, thereby reducing trauma to the patient.

As discussed above, screwing multiple fiducial markers into different locations in the patient's skull 114 results in trauma and/or risk of infection at each one of such multiple different locations. FIG. 8 is a schematic diagram illustrating conceptually, by way of example, but not by way of limitation, a fiducial marker carrier 800 that is attachable to (and also detachable from) a single location on the patient's skull 114, thereby reducing trauma and risk of infection to the patient. In this example, the fiducial marker carrier 800 is configured for carrying multiple different imagable fiducial locators 802 such that they are positioned at different locations about the patient's skull 114. As discussed below, the carrier 800 uses a keyed mounting arrangement, such that the carrier 800 can be attached to the patient's skull 114, then detached from the patient's skull 114, and later reattached to the patient's skull 114 in the same orientation in which it was initially attached to the patient's skull 114.

In the example illustrated in FIG. 8, the carrier 800 includes a keyed frame 804 that is attached to a keyed post 806 for mounting. The keyed post 806 is, in turn, attached to a single flush-mounted or recessed-mounted or other keyed base 808, which was previously screwed into the patient's skull 114. This keyed arrangement of the frame 804, the post 806, and the base 808 permits attachment, detachment, and reattachment in the same orientation as the original attachment, as discussed above. In an alternative example, the post 806 is integrally formed as part of the frame 804, rather than being keyed for attachment thereto.

In one example, such illustrated in FIG. 8, the imagable locators 802 are placed about the subject's head such that they surround the patient's skull. Although such a surrounding arrangement is not required, it is believed to improve the accuracy of using the images of the locators 802 (e.g., in conjunction with the IGS workstation) for planning and/or performing an image-guided surgical procedure, as compared to an arrangements in which locators are disposed more closely together (e.g., on the same side of the subject's head).

Figure 9:
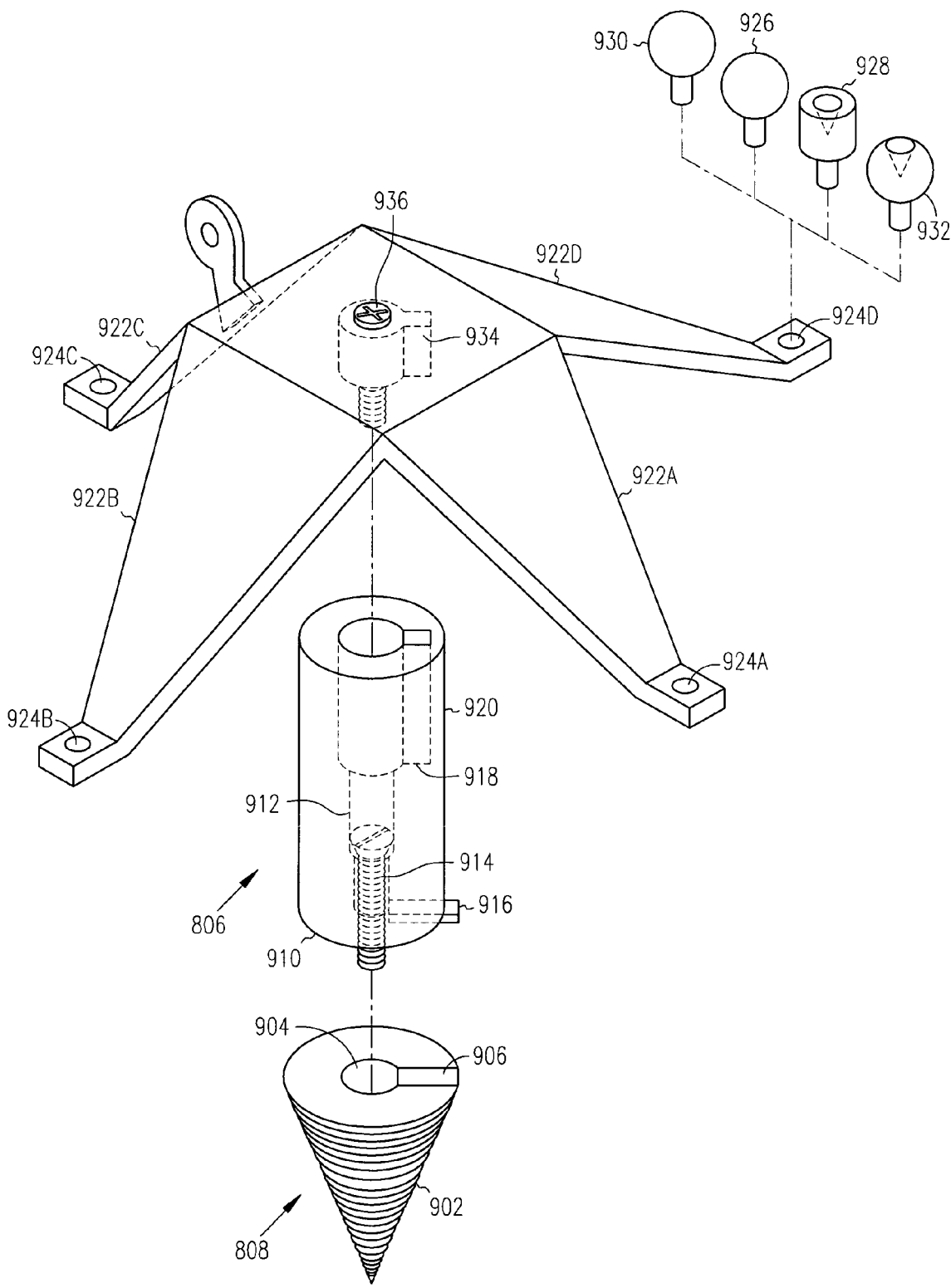
FIG. 9 is an exploded view schematic diagram illustrating generally one example of the carrier, including a frame, a post, and a base.

FIG. 9 is an exploded view schematic diagram illustrating generally, by way of example, but not by way of limitation, one example of the carrier 800, including the frame 804, the post 806, and the base 808. In this example, the base 808 includes self-tapping external threads 902, and is capable of being mounted flush with (or even recessed within) the patient's skull 114. The base 808 includes an internally-threaded receptacle 904 that is sized and otherwise configured such that it is capable of receiving a screw. The base 808 also includes a female or male keying feature for receiving a mating keying feature of the post 806 to fixedly define the orientation of the post 806 with respect to the base 808. In one example, the keying feature includes a key slot 906 extending radially outward from the receptacle 904 along a proximal surface of the base 808.

The post 806 includes a proximal end 908 and a distal end 910. The post 806 includes a center lumen 912 in which an attachment screw 914 is received and seated. The screw 914 attaches the post 806 to the base 808. The distal end 910 of the post 806 includes a male or female keying feature (such as a key protrusion 916 extending radially outward from the center lumen 912 along the distal end 910 of the post 806) that mates with the keying feature (e.g., key slot 906) of the base 808. Such mating during the attachment fixedly defines the orientation of the post 806 with respect to the base 808.

In this example, the center lumen 912 includes a keyed seating receptacle 918 (or an analogous male keyed feature) for receiving a mating keyed feature of the frame 804. In the illustrated example of FIG. 9, the keyed seating receptacle 918 includes an increased diameter of the center lumen 912 (with respect to more distal portions of the center lumen 912) to provide the seating, and a radially-outwardly extending slot 920 to provide the keying.

In the example illustrated in FIG. 9, the frame 804 includes legs 922A-D (or a fewer or greater number of legs 922), such as extending radially outwardly from a hub 924 and downwardly toward the middle portion of the patient's skull. Each of the legs 922 includes, such as at its respective distal end, a threaded receptacle 924A-D (or a snap-fitting or any other coupling) for receiving at least one of an imagable fiducial marker assembly 926, a divot assembly 928, a locator assembly 930 (e.g., reflector, LED, microcoil, etc.) that is remotely detectable by a positioning system in an operating room, or a combination 932 of two or more of the above. In an alternative embodiment (for example where a combination 932 includes an imagable locator and at least one of an operating room position locator and a divot), instantiations of such a combination 932 may be permanently affixed to corresponding locations on the legs 922 of the frame 804.

In the example illustrated in FIG. 9, the hub 924 portion of the frame 804 also includes a downwardly protruding key 934 (or analogous female receptacle) that mates to the keyed seating receptacle 918, of the post 806, into which the key 934 is received. This fixedly defines the orientation of the frame 904 with respect to the post 806. A screw 936 is inserted through the hub 924, the key 934, and into an engaging interior threaded portion of the center lumen 912. This securely attaches the frame 904 to the post 806 in the fixedly defined orientation. The example illustrated in FIG. 9 also includes at least one optional instrument mount 938. In one example, a reference divot (e.g., providing a position reference) is attached to the instrument mount 938.

Although FIGS. 8 and 9 illustrate examples in which a fiducial marker carrier 800 is mounted using a single base 808, in other examples, the carrier may be mounted using two or more bases 808 at the same location on the patient's skull (that is, at adjacent locations within the same scalp incision, or like limited trauma/infection risk zone; the incision need only be large enough to accommodate the two or more bases 808). Using two or more side-by-side bases 808 to attach the post 806 avoids potential rotational misalignment of a single base 808 coming slightly unscrewed from its original position.

Figure 10:
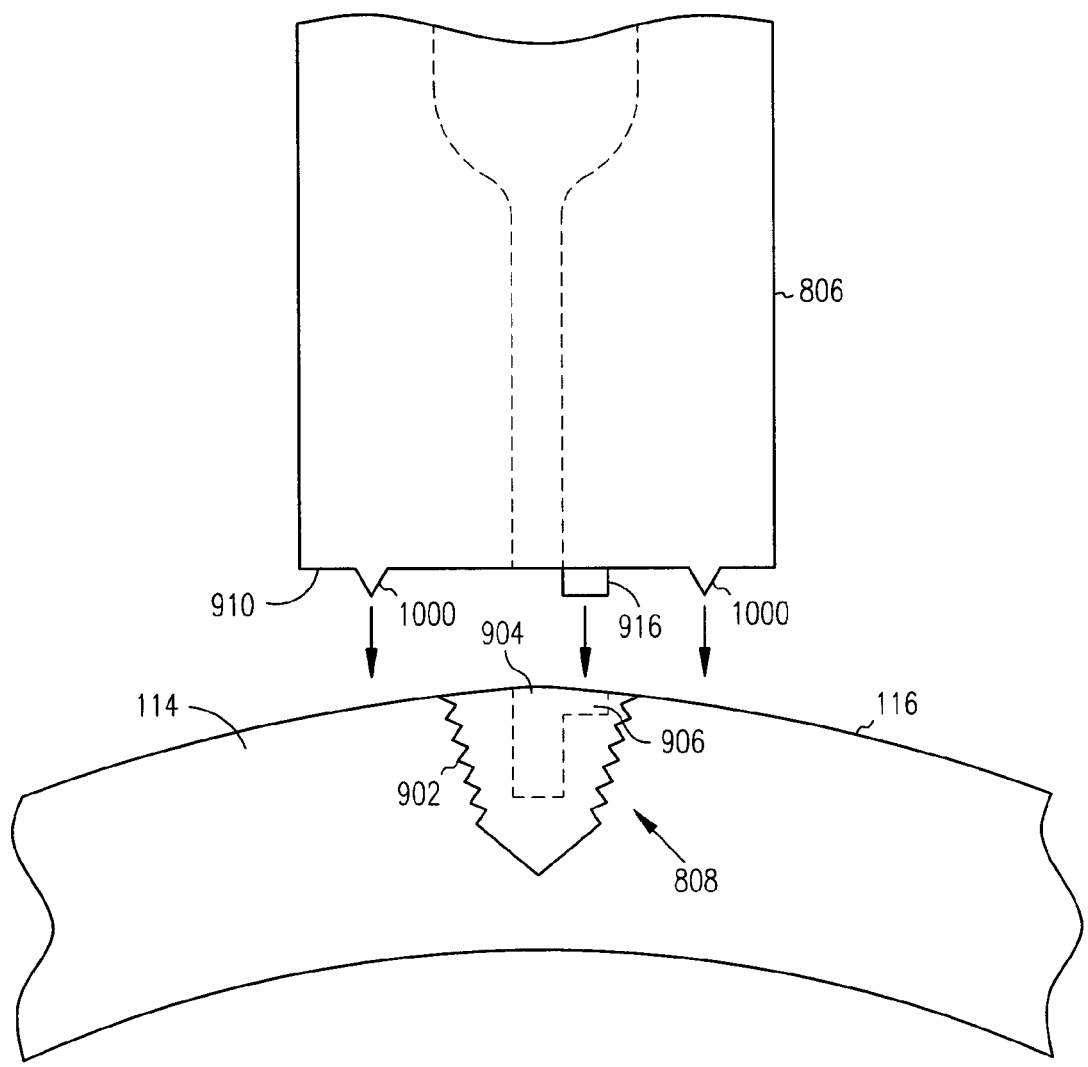
FIG. 10 is a schematic diagram illustrating a portion of a fiducial marker carrier that includes at least one antirotational spike for engaging the surface of the skull.

Alternatively, if a single base 808 is used, such rotational misalignment can be avoided by including one or more anti-rotation spikes 1000 on the bottom of the distal end 910 of the post 806, such as illustrated generally in FIG. 10. In the example illustrated in FIG. 10, the distal end 910 of the post 806 is keyed both to the base 808 and, using the antirotation spike(s) 1000, to indentation(s) made in the surface 116 of the skull 114. However, in an alternative example, the post 806 and the base 808 need not be keyed to each other. Instead, in such an example, the post 806 is keyed only to indentation(s) made by the antirotation spike(s) 1000 in the surface 116 of the skull 114.

In further examples, the various above-described locators (e.g., on the subject's skull, or on a wand, as illustrated in FIG. 3) alternatively or additionally include an electromagnetic (EM) coil that permits determination of the position of the locator using an EM coil detecting positioning system coupled to an IGS workstation rather than the optical positioning system 412 discussed above.

It is to be understood that the above description is intended to be illustrative, and not restrictive. For example, the above-described embodiments may be used in combination with each other. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects.

What is claimed is:

1. An imagable fiducial marker comprising:
   an imaging fluid;
   an imagable portion of a fiducial locator formed only of a substantially solid hygroscopic material configured for soaking up and retaining the imaging fluid via contact with an exterior surface of the imagable portion, wherein the imaging fluid provides a contrast on an image obtained using a first imaging modality; and
   an engaging portion extending from the imagable portion of the fiducial locator and configured to operatively engage into bone;
   wherein the hygroscopic material provides a contrast on an image obtained using a second imaging modality that is different from the first imaging modality.

2. The imagable fiducial marker of claim 1, in which the first imaging modality is magnetic resonance imaging (MRI) and the second imaging modality is computed tomography (CT).

3. The imagable fiducial marker of claim 1, in which the imagable fiducial marker is configured to mount to an anchoring base, the base being sized and shaped to be implanted within a patient's skull such that a top portion of the base is flush to or recessed from an outer surface of the patient's skull.

4. The imagable fiducial marker of claim 3, wherein the engaging portion includes a shaft extending outwardly from the imagable portion of the fiducial locator.

5. The imagable fiducial marker of claim 4, in which the base includes:
   an internal receptacle that is sized and shaped for receiving the shaft; and
   an externally-threaded portion.

6. The imagable fiducial marker of claim 1, in which the imagable portion is substantially spherical.

7. The imagable fiducial marker of claim 1, in which the imagable portion includes a generally cylindrical column.

8. The imagable fiducial marker of claim 7, in which the generally cylindrical column of the imagable fiducial marker is a hexagonal cylindrical column.

9. The imagable fiducial marker of claim 1, in which the imagable fiducial marker is locatable by at least two different imaging modalities.

10. The imagable fiducial marker of claim 1, wherein the hygroscopic material is a solid hygroscopic material that alone is configured to receive and retain the imaging fluid.

11. The imagable fiducial marker of claim 10, wherein the hygroscopic material is at least at an exterior of the imageable portion operable to contact the imaging fluid.

12. The imagable fiducial marker of claim 1, wherein the hygroscopic material is a solid hygroscopic plastic.

13. An apparatus comprising:
    a fiducial marker including:
    an imaging fluid locatable using one or more imaging system modalities;
    a fiducial locator locatable using one or more different imaging system modalities; and
    a shaft extending orthogonally outward from an exterior portion of the fiducial locator, wherein the shaft includes an externally threaded portion at an end;
    wherein the shaft includes a pointed tip;
    wherein the fiducial locator includes a conical divot;
    wherein the fiducial locator is constructed substantially as a solid material that is hygroscopic for receiving and retaining the imaging fluid that is viewable on an imaging system;
    wherein the hygroscopic solid material is exposed and alone retains the imaging fluid;
    wherein the hygroscopic solid material is arranged for imaging using a first modality and the imaging fluid is arranged for imaging using a different second modality;
    wherein each of the solid and the imaging fluid provide contrast for its particular imaging modality.

14. The apparatus of claim 13, further comprising:
    an externally-threaded self-tapping base having an internally threaded receptacle correspondingly sized and shaped to mate with the externally threaded portion of the shaft;
    wherein the externally-threaded self-tapping base is capable of being mounted in a skull either flush to or recessed from an outer surface of the skull.

15. The apparatus of claim 13, wherein the fiducial locator is substantially spherical.

16. An imagable fiducial marker comprising:
    an imaging fluid;
    an imagable portion that is a substantially solid hygroscopic material for receiving and retaining the imaging fluid; and
    a shaft extending orthogonally outward from an exterior surface of the imageable portion, wherein the shaft includes an externally threaded portion at a terminal end of the shaft a distance from the imagable portion;
    wherein the solid hygroscopic material is exposed on an exterior surface of the imagable portion and alone retains the imaging fluid, the hygroscopic material being arranged for imaging using the first modality and the imaging fluid being arranged for imaging using a second modality that is different than the first modality;
    wherein each of the hygroscopic material and the imaging fluid are selected to provide contrast for the respective imaging modality.

17. The imagable fiducial marker of claim 16, wherein the hygroscopic material of the imagable portion is operable to soak up the imaging fluid via contact between an exterior surface of the imagable portion and a volume of the imaging fluid.

18. The imagable fiducial marker of claim 16, wherein the hygroscopic material is at least one of nylon and polyurethane.

19. The imagable fiducial marker of claim 16, further comprising a divot formed in the imagable portion defined by a wall extending into an interior of the imagable portion extending towards an interior of the imagable portion.

20. The imagable fiducial marker of claim 19, wherein the imagable portion is spherical and the divot extends towards a center of the spherical imagable portion.

21. The imagable fiducial marker of claim 19, wherein the imagable portion is cylindrical and the divot extends towards a center of the cylindrical imagable portion.

22. The imagable fiducial marker of claim 16, further comprising an externally-threaded self-tapping base extending between two terminal ends and having an internally threaded receptacle correspondingly sized and shaped to mate with the externally threaded portion of the shaft;
    wherein the externally-threaded self-tapping base is capable of being mounted in a skull with both of the two terminal ends either flush to or recessed below an outer surface of the skull.

* * * * *